United States Patent [19]

Klauser et al.

[11] Patent Number: 4,587,250
[45] Date of Patent: May 6, 1986

[54] THIAZASPIRANE DERIVATIVES, PROCESS FOR THEIR PREPARATION, AND MEDICAMENTS

[75] Inventors: Rainer Klauser; Eike Meinetsberger; Klaüs Bichlmayer, all of Munich, Fed. Rep. of Germany

[73] Assignee: Luitpold-Werk Chemischpharmazeutische Fabrik GmbH & Co., Munich, Fed. Rep. of Germany

[21] Appl. No.: 465,025

[22] Filed: Feb. 8, 1983

[30] Foreign Application Priority Data

Feb. 9, 1982 [DE] Fed. Rep. of Germany ....... 3204373

[51] Int. Cl.$^4$ ................. C07D 277/60; A61K 31/425
[52] U.S. Cl. .................... 514/278; 514/365; 544/54; 546/19; 548/147
[58] Field of Search .......... 548/147; 544/54; 546/19; 514/278, 365

[56] References Cited

U.S. PATENT DOCUMENTS 3,575,204  4/1981  Nakanishi et al. ............. 260/243
3,856,797 12/1974  Arimura et al. ............. 260/293.66

FOREIGN PATENT DOCUMENTS 884875  2/1981  Belgium ..................... 548/147
2828578  1/1979  Fed. Rep. of Germany .......... 277/6

OTHER PUBLICATIONS

March, Advanced Organic Chemistry, p. 703 (1977).
Gyorgydeak, Z., et al., Diketopiperazines from Optically Active Thiazolidine-4-Carboxylic Acids, Chem. Heterocycl. Comp., (1979) 15: 983-988.

Primary Examiner—Robert Gerstl
Attorney, Agent, or Firm—Cooper, Dunham, Clark, Griffin & Moran

[57] ABSTRACT

Novel thiazaspirane derivatives of the general formula

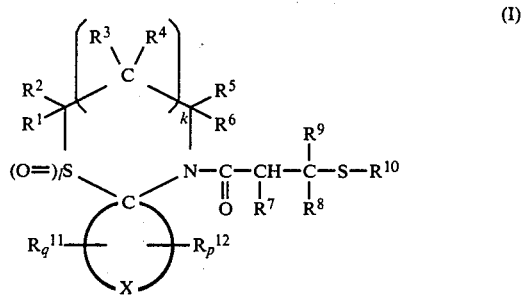

(I)

including salts thereof with physiologically acceptable acids and bases, processes for their preparation and medicaments containing them.

13 Claims, No Drawings

THIAZASPIRANE DERIVATIVES, PROCESS FOR THEIR PREPARATION, AND MEDICAMENTS

The present invention relates to mercaptoacyl derivatives of thiazaspiro compounds, of the general formula

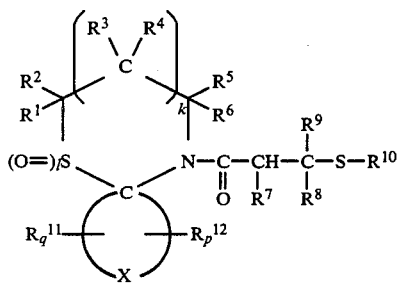
(I)

and salts thereof with physiologically acceptable acids and bases, in which the connecting lines shown in the formula between the spiro-carbon atom and X are lower alkylene groups of identical or different chain lengths, and the X-containing ring thereby formed contains from 4 to 8 ring members and X can occupy any position within this ring, with the exception of the positions immediately adjacent to the spiro-carbon atom, $R^1$, $R^2$, $R^3$, $R^4$, $R^5$, $R^8$ and $R^9$ independently of one another are hydrogen, lower alkyl, lower alkenyl, aryl, aryl-lower alkyl, cycloalkyl, bridged cycloalkyl or trifluoromethyl, $R^6$ has the same meanings as $R^1$ or is

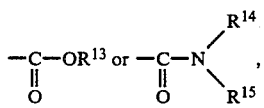

in which $R^{13}$, $R^{14}$ and $R^{15}$ independently of one another are hydrogen, lower alkyl, aryl, aryl-lower alkyl, cycloalkyl or bridged cycloalkyl, or carboxymethyl which is unsubstituted or substituted by lower alkyl, aryl, aryl-lower alkyl, amino-lower alkyl, guanidino-lower alkyl, carboxy-lower alkyl, hydroxy-lower alkyl, mercapto-lower alkyl or (3-indolyl)-lower alkyl, $R^7$ is hydrogen, halogen, trifluoromethyl, lower alkyl, lower alkenyl, aryl, aryl-lower alkyl, cycloalkyl or bridged cycloalkyl, $R^{10}$ is hydrogen, lower alkyl, lower alkenyl, aryl, aryl-lower alkyl, cycloalkyl, bridged cycloalkyl, lower alkanoyl, aroyl, aryl-lower alkanoyl, aryl-lower alkenoyl, $R^{16}$, A or B, and A is

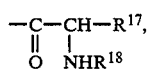

B is

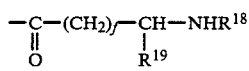

and $R^{16}$ corresponds to the formula II

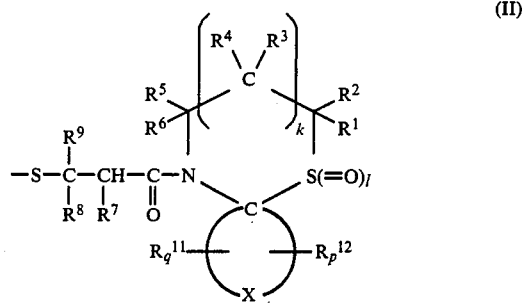

and in which $R^{17}$ is hydrogen, lower alkyl, aryl, aryl-lower alkyl, amino-lower alkyl, guanidino-lower alkyl, carboxy-lower alkyl, hydroxy-lower alkyl, mercapto-lower alkyl or (3-indolyl)-lower alkyl, $R^{18}$ is hydrogen, lower alkyl, aryl, aryl-lower alkyl, cycloalkyl, bridged cycloalkyl, lower alkanoyl, aroyl, aryl-lower alkanoyl, cycloalkanoyl or a conVentional protective group (which can be detached again) for amino groups, $R^{19}$ has the same meanings as $R^6$ and f is 0, 1, 2 or 3, $R^{11}$ and $R^{12}$ independently of one another are hydrogen, hydroxyl, halogen, trifluoromethyl, lower alkyl, aryl, aryl-lower alkyl, cycloalkyl, bridged cycloalkyl, lower alkanoyl, aroyl, aryl-lower alkanoyl, lower alkoxy, aryloxy, aryl-lower alkoxy,

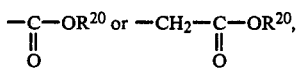

in which $R^{20}$ has the same meanings as $R^{13}$, and $R^{11}$ and $R^{12}$ are bonded to any desired position Of the X-containing ring, with the exception of X, or $R^{11}$ and $R^{12}$ are lower alkylene which bridges the X-containing ring, the bridged ring system containing 5 to 12 ring carbon atoms, or $R^{11}$ and $R^{12}$ are lower alkylene which forms a carbocyclic ring of 3 to 8 carbon atoms which is fused onto the X-containing ring, X is oxygen, sulfur,

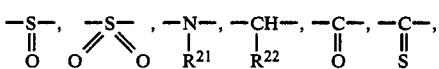

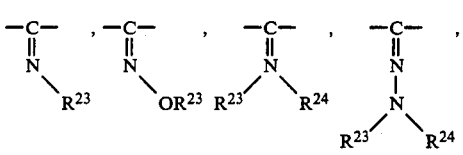

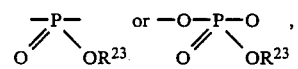

in which $R^{21}$ is hydrogen, lower alkyl, lower alkenyl, aryl, aryl-lower alkyl, cycloalkyl, bridged cycloalkyl, lower alkanoyl, aroyl, aryl-lower alkanoyl, aryl-lower alkenoyl or cycloalkanoyl, $R^{22}$ is hydrogen, halogen, trifluoromethyl, lower alkyl, aryl, aryl-lower alkyl, cycloalkyl, lower alkanoyl, aroyl, aryl-lower alkanoyl, $-OR^{23}$,

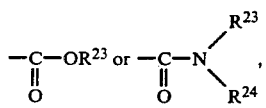

$R^{23}$ and $R^{24}$ independently of one another are hydrogen, lower alkyl, aryl, aryl-lower alkyl or cycloalkyl, k and l independently of one another are 0, 1 or 2, and q and p independently of one another are 0, 1, 2, 3 or 4, with the proviso that, if k, l, p and q are at the same time zero, $R^1$, $R^2$ and $R^5$ are at the same time hydrogen and X is

$R^{22}$ is other than hydrogen.

These compounds according to the invention are active ingredients with surprisingly useful pharmacological properties, which are listed below.

The following explanations relate to the various substituents and radicals (in the various formulae given) mentioned in connection with the present invention and description:

Examples of lower alkyl radicals are straight-chain or branched, saturated alkyl radicals of not more than 6 carbon atoms, especially methyl, ethyl, n-propyl, n-butyl, n-pentyl, n-hexyl, isopropyl, isobutyl, tert.-butyl and neopentyl, and preferably methyl, ethyl, n-propyl, isopropyl, tert.-butyl and n-butyl.

Examples of lower alkenyl radicals are unsaturated hydrocarbon radicals of 2 to 6 carbon atoms, e.g. vinyl, allyl and 1-propen-2-yl, preferably allyl.

Examples of lower alkylene radicals are straight-chain or branched alkylene radicals of not more than 6 carbon atoms, especially methylene, ethylene, propylene, butylene, pentylene, hexylene, methylmethylene, methylethylene and dimethylmethylene, and preferably methylene, ethylene, propylene, butylene, methylethylene and dimethylmethylene.

Where $R^{11}$ and $R^{12}$ are lower alkylene which forms a bridged ring system with the X-containing ring, X is not a bridgehead and the bicyclic ring systems formed contain 5 to 12 ring carbon atoms. The norbornyl system, the bornyl system and the N-methyl-8-azabicyclo[3.2.1]octane system are preferred.

Where $R^{11}$ and $R^{12}$ are lower alkylene which forms a fused carbocyclic ring with the X-containing ring, the linkage positions are vicinal. X is never a linking position and the fused-on ring thus formed contains from 3 to 8 ring carbon atoms. The cyclopropane, cyclopentane and cyclohexane ring are preferred.

Examples of cycloalkyl radicals are saturated or unsaturated radicals of cyclic hydrocarbons of 3 to 12 carbon atoms which are unsubstituted or are mono- or di-substituted by methyl, ethyl, isopropyl or tert.-butyl, especially cyclopropyl, cyclobutyl, cyclopentyl, cyclohexyl, cycloheptyl, cyclopentenyl, cyclohexenyl, cyclooctenyl, ethylcyclopropyl, methylcyclopentyl, methylcycloheptyl, dimethylcyclohexyl and tert.-butylcyclohexyl, and particularly preferably cyclopentyl, cyclohexyl and cyclopropyl.

Examples of bridged cycloalkyl radicals are bridged hydrocarbon radicals of 5 to 10 carbon atoms, e.g. bornyl, isobornyl, norbornyl and adamantyl, and preferably norbornyl, bornyl and adamantyl.

Examples of aryl radicals are unsubstituted phenyl or phenyl which is mono-, di- or tri-substituted by lower alkyl, hydroxyl, lower alkoxy, lower alkanoyloxy, guanidino, amino, lower alkylamino, lower alkanoylamino, carboxyl, lower alkoxycarbonyl, N-amidinocarboxamide, halogen, trifluoromethyl or nitro, and naphthyl. Lower alkyl and lower alkanoyl have the meanings given in this description.

Unsubstituted phenyl and phenyl which is mono- or di-substituted by the above substituents are preferred. PhenyL, 4-methylphenyl, 2-methylphenyl, 4-methoxyphenyl, 2-methoxyphenyl, 2-acetoxyphenyl, 4-hydroxyphenyl, 2-hydroxyphenyl, 3-hydroxyphenyl, 4-aminophenyl, 4-dimethylaminophenyl, 4-N-acetylaminophenyl, 3-trifluoromethylphenyl, 4-carboxyphenyl, 4-N-amidinocarboxamidophenyl, 4-chlorophenyl, 2-chlorophenyl, 2-fluorophenyl, 4-fluorophenyl, 3,5-dichlorophenyl, 2,4-dimethylphenyl, 3,5-dihydroxyphenyl and 2,4-dihydroxyphenyl are particularly preferred.

Aryl and lower alkyl in aryl-lower alkyl have the above meanings, and the aryl radical can be bonded to any desired position of the lower alkyl group. Preferred representatives are radicals in which phenyl radicals which are unsubstituted or mono- or di-substituted by amino, lower alkylamino, hydroxyl, lower alkoxy, lower alkyl or halogen are bonded to lower alkyl radicals of not more than 4 carbon atoms. 2-Phenethyl, 4-phenylbutyl, 2-phenylbutyl, 2-phenylpropyl, 3-phenylpropyl, benzyl, 4-hydroxybenzyl, 4-methoxybenzyl, 4-aminobenzyl, 4-fluorobenzyl, 3,5-dichlorobenzyl, 2,4-dimethoxybenzyl and 2,4-dimethylbenzyl are particularly preferred.

Examples of lower alkanoyl radicals are straight-chain or branched saturated radicals of aliphatic carboxylic acids of not more than 6 carbon atoms, especially formyl, acetyl, propanoyl, butanoyl, pentanoyl, capronyl, isobutanoyl and pivaloyl. Acyl radicals of not more than 4 carbon atoms, especially formyl, acetyl, propanoyl, butanoyl and isobutanoyl, are preferred.

Examples of lower alkenoyl radicals are straight-chain or branched radicals of unsaturated aliphatic carboxylic acids of 3 to 8 carbon atoms, e.g. acryloyl, methacryloyl, 2,3-dimethylacryloyl, vinylacetyl and crotonyl. Lower alkenoyl radicals of 3 or 4 carbon atoms, especially acryloyl and vinylacetyl, are preferred.

Examples of cycloalkanoyl radicals are radicals of cycloaliphatic carboxylic acids of 5 to 12 carbon atoms, e.g. cyclobutanoyl, cyclopentanoyl, cyclohexanoyl and bornylcarbonyl, preferably cyclopentanoyl and cyclohexanoyl.

Aryl and lower alkanoyl in aryl-lower alkanoyl have the above meanings, and the aryl radical can be bonded to any desired position of the lower alkanoyl radical. Preferred representatives are radicals with not more than 4 carbon atoms in the lower alkanoyl group, especially phenylacetyl, 2-phenylpropanoyl, 3-phenylpropanoyl, 4-phenylbutanoyl and 2-phenylbutanoyl.

Aryl and lower alkenoyl in aryl-lower alkenoyl have the above meanings, and the aryl radical can be bonded to any desired position of the lower alkenoyl radical. Preferred representatives are radicals with 3 or 4 carbon atoms in the lower alkenoyl radical, and cinnamoyl is particularly preferred.

Examples of aroyl radicals are radicals of aromatic carboxylic acids such as benzoic acid, α-naphthoic acid and β-naphthoic acid. The benzoic acid radicals can be unsubstituted or substituted by halogen, lower alkyl, hydroxyl, lower alkoxy, carboxyl, amino, lower alkylamino, lower alkanoylamino, guanidino, amidino, trifluoromethyl, nitro, lower alkoxycarbonyl or lower alkanoyloxy. Lower alkyl and lower alkanoyl have the meanings given in this description. Benzoyl radicals which are unsubstituted or substituted by the substituents just mentioned are preferred, and benzoyl, 2-acetoxybenzoyl, 4-dimethylaminobenzoyl, 4-N-acetylaminobenzoyl, 4-methylbenzoyl, phthaloyl, 4-methoxybenzoyl and 3-chlorobenzoyl are particularly preferred.

Examples of halogen atoms are fluorine, chlorine, bromine and iodine. Fluorine and chlorine are preferred.

Examples of the protective groups mentioned for $R^{18}$ are the protective groups which are conventional for amino groups in peptide chemistry, especially those which can be detached by hydrolysis or hydrogenolysis. tert.-Butoxycarbonyl, benzyloxycarbonyl, trifluoroacetyl, methylsulfonylethoxycarbonyl and 9-fluorenylmethoxycarbonyl are preferred.

The compounds represented by formula I are spiroring systems, and the connecting lines shown in the formula between the spiro-carbon atom and X are each an unsubstituted or substituted lower alkylene radical. These lower alkylene radicals can be of identical or different chain lengths and have the above meanings. Examples of X-containing rings are rings with from 4 to 8 ring members, preferably with 5 or 6 ring members. The 4-tetrahydropyran, 4-tetrahydrothiopyran, 4-piperidine, cyclohexane, 3-tetrahydropyran, 3-tetrahydrothiopyran, 3-piperidine, 3-oxolane, 3-thiolane, cyclopentane and 3-pyrrolidine rings are particularly preferred.

Where $R^7$ in the compounds according to the invention is other than hydrogen (=$R^{7'}$), the compounds are optically active compounds of the formula I a

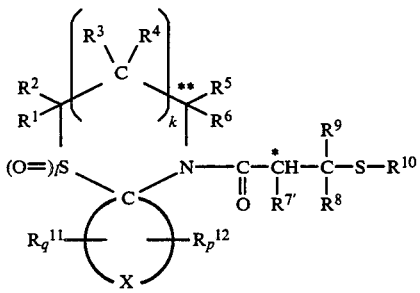

(I a)

in which the carbon atom which carries $R^{7'}$ and is labeled * here is the optically active center.

The carbon atom carrying $R^5$ and $R^6$ can be another optically active center, which is of importance for the compounds according to the invention. In formula I a, this carbon atom is labeled **. The compounds according to the invention can be in the R-, S- and RS-form in each of the two centers independently of one another. The formula I in claim 1 comprises both the R-form, the S-form and the racemic mixture, i.e. the RS-form, of the particular optically active centers of the compounds according to the invention. In the optically active center labeled *, the S-form is generally preferred. In the optically active center labeled **, the R-form is generally preferred.

The compounds according to the invention can moreover contain other optically active centers as a result of the presence of substituents $R^1$, $R^2$, $R^3$, $R^4$, $R^8$, $R^9$, $R^{11}$ and $R^{12}$. Likewise, one or more of the substituents $R^1$ to $R^{24}$ may possess a center of asymmetry.

Where the compounds of the formula I are acidic, the invention also relates to the salts of the acids of the formula I with physiologically acceptable inorganic and organic bases, for example the ammonium, sodium, potassium, lithium, magnesium, calcium, ethanolamine, triethanolamine, morpholine and piperidine salts.

Where the compounds according to the invention are basic, the invention also relates to the salts of the bases of the formula I with physiologically acceptable inorganic and organic acids, for example the chlorides, acetates, carbonates, tartrates, citrates, formates, lactates and stearates. Chlorides, acetates, citrates and tartrates are particularly preferred.

The compounds according to the invention can be synthesized by processes similar to the various processes known from the literature.

Method 1

One possibility comprises reacting a carboxylic acid of the general formula III

(III)

with a thio compound of the general formula IV

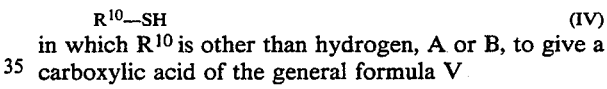

(IV)

in which $R^{10}$ is other than hydrogen, A or B, to give a carboxylic acid of the general formula V

(V)

This reaction is carried out in a conventional manner in the presence or absence of an organic solvent, e.g. carbon tetrachloride, chloroform or toluene, and in the presence or absence of a free radical initiator, e.g. azobis-isobutyronitrile. These methods are described in Houben-Weyl, Methoden der Organischen Chemie, Volume IX, 1955, page 120 et seq. and page 750 et seq.

The carboxylic acid of the general formula V is then reacted with a thiazaspiro compound of the general formula VI

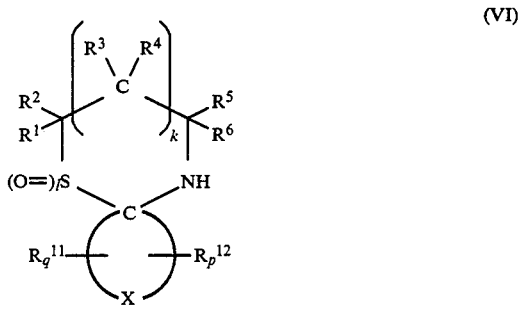

(VI)

to give an acid amide of the general formula I. Where relevant, this reaction can be carried out in the presence of a coupling reagent, e.g. dicyclohexylcarbodiimide, or after suitable activation of the acid group of the carboxylic acid of the formula V. Examples of methods of activating the acid group are conversion into an acid halide, conversion into a mixed anhydride by means of isobutyl chloroformate, and conversion into an activated ester by means of N-hydroxysuccinimide. Examples of such acylation processes are described in Houben-Weyl, Methoden der Organischen Chemie, Volume XV, Section II (1974), page 1 et seq. The preferred reaction is conversion of a carboxylic acid of the formula V into an acid halide and subsequent reaction of the acid halide with a thiazaspiro compound of the formula VI in the presence of, in particular, an equivalent amount of a base, e.g. an alkali metal carbonate, alkali metal bicarbonate or alkali metal hydroxide, triethylamine or Hünig base, in an organic solvent, e.g. methylene chloride, acetonitrile, chloroform, dioxane or tetrahydrofuran, or in aqueous solution. A compound of the general formula I in which $R^{10}$ is other than hydrogen, A or B is obtained.

If desired, the resulting compound of the general formula I in which $R^{10}$ is other than hydrogen, A or B can be converted into a compound of the formula I in which $R^{10}$ is hydrogen. Where $R^{10}$ is lower alkanoyl, aroyl, aryl-lower alkanoyl or aryl-lower alkenoyl, this conversion is carried out in a conventional manner by treatment with an inorganic or organic base, for example with an aqueous solution of a base, such as sodium hydroxide solution, potassium hydroxide solution, aqueous ammonia solution or an aqueous solution of triethylamine or ethanolamine. 5–25% strength aqueous ammonia solution is preferably used. The reaction is carried out at from 0° C. to 100° C., preferably at from 0° to 30° C. Where $R^{10}$ in a compound of the formula I is lower alkyl, lower alkenyl, cycloalkyl, bridged cycloalkyl, aryl, aryl-lower alkyl or $R^{16}$, the conversion to a compound of the formula I where $R^{10}$ is hydrogen is carried out by hydrogenolysis, for example by reaction with an alkali metal in liquid ammonia or in an organic amine. Examples of suitable organic amines are methylamine, dimethylamine and pyridine, and examples of alkali metals which can be used are lithium, sodium and potassium. Reaction with sodium in liquid ammonia is preferred.

If desired, the resulting compounds of the formula I in which $R^{10}$ is hydrogen can be converted into a compound of the general formula I in which $R^{10}$ is A or B, for example by reaction with an aminoacid of the formula A—OH or B—OH, in which A and B have the above meanings.

Protected aminoacids which carry, on the nitrogen atom, acetyl, benzoyl or a protective group which is conventional in peptide chemistry, e.g. tert.-butoxycarbonyl, benzyloxycarbonyl, 9-fluorenylmethoxycarbonyl or methylsulfonylethoxycarbonyl, are preferred.

Where $R^{17}$ or $R^{19}$ in A—OH or B—OH is a functional radical as defined in claim 1 (e.g. amino-lower alkyl, hydroxy-lower alkyl, carboxy-lower alkyl or mercapto-lower alkyl), these radicals may also, where relevant, carry suitable protective groups, such as those which are conventional in peptide chemistry and are described, for example, in "The Peptides", Volume 3, edited by E. Gross and J. Meienhofer, 1981, Academic Press. Preferred protective groups are benzyloxycarbonyl, for amino groups, benzyl and methyl, for acid groups, benzyloxycarbonyl and trimethylsilyl, for hydroxyl groups, and benzyl, for mercapto groups.

The reaction of a compound I in which $R^{10}$ is hydrogen with an acid A—OH or B—OH is carried out after suitable activation of the carboxyl group of A—OH or B—OH in a conventional manner, such as is described under Method 1.

Where relevant, when the reaction has ended, the protective groups on the functional radicals $R^{17}$ or $R^{19}$ in A or B can be split off by a suitable hydrolysis or hydrogenolysis reaction in order to obtain a compound of the formula I. An example of a hydrolysis process is hydrolysis in an aqueous acid or base. Hydrogenolysis is preferably carried out by catalytic hydrogenation, in particular hydrogenation on palladium sponge.

If desired, an ester of the general formula I, i.e. a compound in which $R^6$ is

$R^{11}$ or $R^{12}$ is

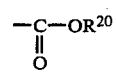

or X is

and $R^{13}$, $R^{20}$ and $R^{23}$ are each other than hydrogen, can be converted into a free acid in a conventional manner, for example by hydrolysis with an aqueous solution of an inorganic or organic base, e.g. sodium hydroxide solution, potassium hydroxide solution, ammonia or triethylamine, or with a dilute aqueous acid, e.g. hydrochloric acid, sulfuric acid, formic acid or acetic acid. Hydrolysis with dilute sodium hydroxide solution is generally preferred.

If desired, a salt with a physiologically acceptable base can be prepared from the free acid in a conventional manner, preferably by reaction of the carboxylic acid of the formula I with an equivalent amount of an inorganic or organic base in a solvent in which the salt is sparingly soluble, and isolation of the salt by filtration, or by reaction in aqueous solution and isolation of the salt by lyophilization. Examples of inorganic and organic bases which can be used are lithium hydroxide, sodium hydroxide, potassium hydroxide, magnesium hydroxide, calcium hydroxide, ammonia, ethanolamine, triethanolamine, morpholine and piperidine.

A basic compound of the general formula I according to the invention can be converted into a salt with a physiologically acceptable inorganic or organic acid in a conventional manner, preferably by reacting the base of the formula I with an equivalent amount of the acid in a solvent in which the salt is sparingly soluble and isolating the salt by filtration, or by reaction in an aqueous medium and isolation of the salt by lyophilization. Examples of suitable inorganic and organic acids are hydrogen chloride, carbonic acid, acetic acid, formic acid, tartaric acid, citric acid, lactic acid and stearic acid.

Compounds of the formula I a according to the invention are optically active. In the context of the invention, two optically active centers are of importance, i.e.

the carbon atom carrying $R^5$ and $R^6$ and the carbon atom carrying $R^{7'}$.

Compounds of the formula I a are generally prepared from optically active starting compounds VI a

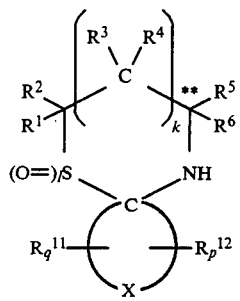
(VI a)

which are known or can be prepared in a conventional manner and are generally in the optically pure R- or S-form at the asymmetric carbon atom labeled . During preparation of the compounds of the general formula I a, the configuration at this carbon atom does not change. The absolute configuration of the compounds of the formula I a at the carbon atom labeled  is thus determined by the choice of starting compound VI a.

The configuration of compounds of the formula I a, according to the invention, at the carbon atom carrying $R^{7'}$ is determined by the choice of the corresponding carboxylic acid of the general formula V a

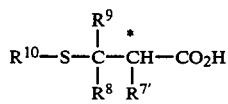
(Va)

This carboxylic acid can be in the R-form, in the S-form and as a racemic mixture, i.e. in the RS-form, at the carbon atom labeled *.

In the procedure according to Method 1, a racemic mixture of the carboxylic acid of the formula V a is generally obtained. If desired, this racemic mixture can be split into its optical antipodes in a conventional manner, for example by reaction of the carboxylic acid V a to give a salt with an optically active base, fractional crystallization of the diastereomeric salts and isolation of the optically active carboxylic acid of the formula V a by acidification of the aqueous solution of the diastereomeric salt and extraction with an organic solvent. Examples of suitable bases are ephedrine, 1-phenethylamine, amine, brucine and cinchonidine, preferably brucine and cinchonidine. The salts are recrystallized from a suitable organic solvent, e.g. dimethylformamide, tetrahydrofuran or acetonitrile, preferably acetonitrile. Alternatively, a compound of the formula V a can be separated into its optical antipodes by chromatography on a suitable stationary phase, for example by chromatography on polystyrene, to which L-proline is covalently bonded. The further reaction with a compound of the formula VI a is thus carried out with a carboxylic acid of the formula V a in which the carbon atom carrying $R^{7'}$ is specifically in the R-form, S-form or RS-form. The configuration at this optically active carbon is retained during the reaction to give a compound of the formula I a. The compound of the general formula I a is thus obtained with a specific configuration at the two carbon atoms labeled * and **.

Method 2

The compounds of the general formula I can also be prepared by a second method similar to processes which are known from the literature. This method comprises reacting a monounsaturated carboxylic acid of the general formula III

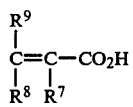
(III)

in which $R^7$, $R^8$ and $R^9$ have the meanings given in claim 1, with a thiazaspiro compound of the general formula VI

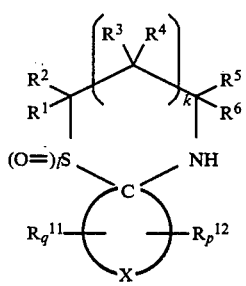
(VI)

to give an acid amide. This reaction is carried out after suitable activation of the acid group of the carboxylic acid of the formula III. The methods of activation and reaction are described in detail under Method 1. A product of the general formula VII

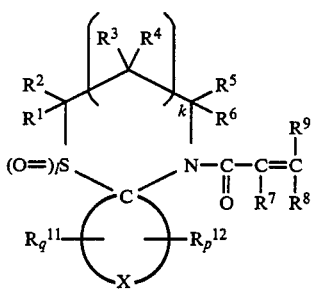
(VII)

in which $R^1$ to $R^{12}$, k, l, q, p and x have the meanings given in claim 1, is thereby obtained.

The compound of the general formula VII is then reacted with a thio compound of the general formula IV

$R^{10}$—SH   (IV)

in which $R^{10}$ is other than hydrogen, A or B, in the presence or absence of an organic solvent, e.g. ethanol, methanol, chloroform, carbon tetrachloride or toluene, and in the presence or absence of a free radical initiator, e.g. azo-bis-isobutyronitrile, to give a compound of the general formula I. At this point, Method 2 becomes the same as Method 1.

Where a compound of the general formula I a

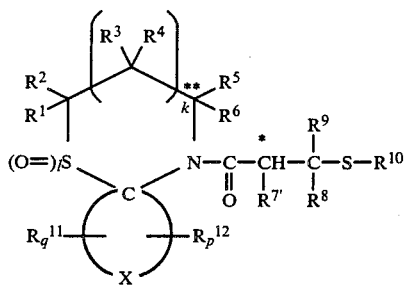 (Ia)

is obtained in the preparation according to Method 2, the configuration at the asymmetric carbon atom labeled ** is determined by the choice of starting compound VI a, as explained under Method 1. The configuration at the carbon atom carrying $R^{7'}$ and labeled * is generally the racemic RS-form in the procedure of Method 2. This is the case if a carboxylic acid of the formula III a

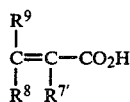 (IIIa)

in which $R^{7'}$ has the meanings given in claim 1, with the exception of hydrogen, is reacted with a thiazaspiro compound of the formula VI a, and the subsequent procedure is as described above.

If desired, a compound of the general formula I a in which the configuration at the carbon atom carrying $R^{7'}$ is the RS-form can be split into its optical antipodes in a conventional manner, as described under Method 1. Since compounds of the general formula I a contain another center of asymmetry as a result of the carbon atom carrying $R^6$, these compounds are diastereomers. The diastereomers can also be separated directly by conventional fractional crystallization or a suitable chromatographic method. A compound of the general formula I a in which the configuration at each of the two centers of asymmetry is the R-form or the S-form is thereby obtained.

The compounds of the general formula T can moreover be prepared by processes similar to other processes known from the literature. In particular, the carboxylic acids of the general formula V

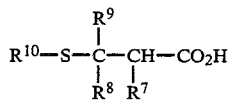 (V)

can be prepared by further generally known routes. For exampLe, a carboxyLic acid of the general formula VIII

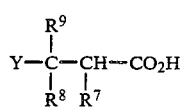 (VIII)

in which Y is halogen, can be reacted with a thio compound of the formula IV $$R^{10}-SH \quad \text{(IV)}$$

in which $R^{10}$ is other than hydrogen, A or B, to give a carboxylic acid of the general formula V in which $R^{10}$ is other than hydrogen, A or B, or a thio compound of the formula IV can be allowed to act on a lactone of the formula IX

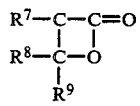 (IX)

in order to obtain a carboxylic acid of the general formula V.

The starting compounds of the general formulae III, IV, VIII, IX and III a mentioned in Methods 1 and 2 are known, or they can be prepared in a conventional manner.

The starting compounds of the general formulae VI and VI a are prepared by processes similar to those described in the following literature:

Ratner, S. and Clarke, H. T. (1937), J. Amer. Chem. Soc. 59, 200, Riemschneider, R. and Hoyer, G. A. (1962), Z. Naturforsch. 17 B, 765 and Ramontian, E., Balog, A. and Deesy, A. (1963), Acad. Rep. Pop. Rom., Filiala Cluj, Studii Cercetari Chim. 14, 321.

For example, an aminothio compound, e.g. cysteamine, L-cysteine, D-cysteine, 3-phenyl-L-cysteine, D-penicillamine, L-penicillamine or homocysteine, is reacted with a cyclic ketone, e.g. tetrahydropyran-4-one, tetrahydrothiopyran-4-one, N-methylpiperid-4-one, 4-carboxycyclohexanone or 2-ethoxycarbonyl-cyclohexanone, in an organic or inorganic solvent, e.g. water, ethanol, an ethanol/water mixture or toluene, for example by stirring the components for from 1 to 10 hours, preferably from 1 to 5 hours, at, for example, from 0° C. to 180° C., preferably from 40° C. to 150° C. A compound of the formula VI in which l is zero is thus obtained.

If desired, a compound of the formula VI in which l is zero can be oxidized to a compound of the formula VI in which l is one by treating VI by one of the processes described in the following literature: Leonard, N. J., Johnson, C. R. (1962) J. Org. Chem. 27, 282.

If desired, a compound of the formula VI in which l is zero can be oxidized to a compound of the formula VI in which l is two by treating VI by one of the processes described in the following literature: Fehnel, E. A., Carmack, M. (1948) J. Amer. Chem. Soc. 70, 1813 and Arndt, F., Bekir, N. (1930) Chem. Ber. 63, 2390.

Compounds of the following general formula VI' are novel compounds which are useful intermediates for the preparation of compounds of the formula I. The present invention thus also relates to the compounds of the general formula VI'

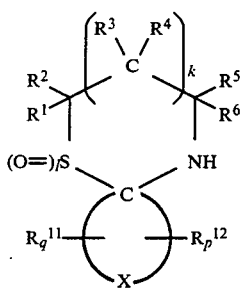

in which $R^1$, $R^2$, $R^3$, $R^4$, $R^5$, $R^6$, $R^{11}$, $R^{12}$, X, k, t, p and q have the meanings given in claim 1, with the proviso that, if l and q are zero, p is zero or one, $R^{12}$ is aryloxy and X is

then $R^{22}$ is other than hydrogen, and with the proviso that if the X-containing ring has six ring members, then X is other than

The process for the preparation of the compounds of the formula VI' is analogous to that described above in connection with the preparation of compounds of the formulae VI and VI a. An aminothio compound of the formula X

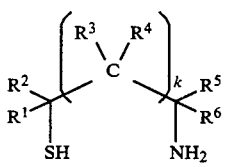

is reacted with a cyclic ketone of the formula XI

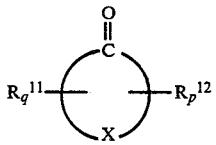

to give a compound of the formula VI' in which l is zero and the remaining substituents and indices have the meanings given above in connection with formula VI'. The reaction conditions are similar to those described in connection with the preparation of VI and VI a. Oxidation to compounds of the formula VI' in which l is one or two is carried out, where relevant, by processes similar to those described in connection with the preparation of the compounds VI and VI a. The present invention also relates to this preparation of compounds of the formula VI' from compounds of the formulae X and XI.

The following compounds of the general formula I are particularly preferred:

1. N-[(2R,S)-3-Acetylthio-2-methylpropanoyl]-(3R)-1,8-dithia-4-azaspiro[4.5]decane-3-carboxylic acid
2. N-[(2S)-3-Acetylthio-2-methylpropanoyl]-(3R)-1,8-dithia-4-azaspiro[4.5]decane-3-carboxylic acid and the corresponding (2R)-compound
3. N-[(2R,S)-3-Mercapto-2-methylpropanoyl]-(3R)-1,8-dithia-4-azaspiro[4.5]decane-3-carboxylic acid
4. N-[(2S)-3-Mercapto-2-methylpropanoyl]-(3R)-1,8-dithia-4-azaspiro[4.5]decane-3-carboxylic acid and the corresponding (2R)-compound
5. (3R, 3'R)-4,4'-[3,3'-Dithiobis[(2R,S)-2-methylpropanoyl]]-bis-(1,8-dithia-4-azaspiro[4.5]decane-3-carboxylic acid)
6. N-[(2R,S)-3-Acetylthio-2-methylpropanoyl]-(3R)-8-oxa-1-thia-4-azaspiro[4.5]decane-3-carboxylic acid
7. N-[(2S)-3-Acetylthio-2-methylpropanoyl]-(3R)-8-oxa-1-thia-4-azaspiro[4.5]decane-3-carboxylic acid and the corresponding (2R)-compound
8. N-[(2R,S)-3-Mercapto-2-methylpropanoyl]-(3R)-8-oxa-1-thia-4-azaspiro[4.5]decane-3-carboxylic acid
9. N-[(2S)-3-Mercapto-2-methylpropanoyl]-(3R)-8-oxa-1-thia-4-azaspiro[4.5]decane-3-carboxylic acid and the corresponding (2R)-compound
10. (3R, 3'R)-4,4'-[3,3'-Dithiobis[(2S)-2-methylpropanoyl]]-bis-(8-oxa-1-thia-4-azaspiro[4.5]decane-3-carboxylic acid
11. 4-[(2R,S)-3-Acetylthio-2-methylpropanoyl]-(3R)-8-methyl-1-thia-4,8-diazaspiro[4.5]decane-3-carboxylic acid
12. 4-[(2R,S)-3-Mercapto-2-methylpropanoyl]-(3R)-8-methyl-1-thia-4,8-diazaspiro[4.5]decane-3-carboxylic acid
13. 4-[(2S)-3-Acetylthio-2-methylpropanoyl]-(3R)-8-methyl-1-thia-4,8-diazaspiro[4.5]decane-3-carboxylic acid and the corresponding (2R)-compound
14. 4-[(2S)-3-Mercapto-2-methylpropanoyl]-(3R)-8-methyl-1-thia-4,8-diazaspiro[4.5]decane-3-carboxylic acid and the corresponding (2R)-compound
15. Methyl N-[(2R,S)-3-acetylthio-2-methylpropanoyl]-(3R)-8-phenyl-1-thia-4-azaspiro[4.5]decane-3-carboxylate and the corresponding (2R)-compound and (2S)-compound
16. Methyl N-[(2R,S)-3-mercapto-2-methylpropanoyl]-(3R)-8-phenyl-1-thia-4-azaspiro[4.5]decane-3-carboxylate and the corresponding (2R)-compound and (2S)-compound
17. 4-[(2R,S)-3-Acetylthio-2-methylpropanoyl]-(3R)-8-benzoyl-1-thia-4,8-diazaspiro[4.5]decane-3-carboxylic acid and the corresponding (2R)-compound and (2S)-compound
18. 4-[(2R,S)-3-Mercapto-2-methylpropanoyl]-(3R)-8-benzoyl-1-thia-4,8-diazaspiro[4.5]decane-3-carboxylic acid and the corresponding (2R)-compound and (2S)-compound
19. 4-[(2R,S)-3-Acetylthio-2-methylpropanoyl]-(3R)-8-acetyl-1 -thia-4,8-diazaspiro[4.5]decane-3-carboxylic acid and the corresponding (2R)-compound and (2S)-compound
20. 4-[(2R,S)-3-Mercapto-2-methylpropanoyl]-(3R)-8-acetyl-1-thia-4,8-diazaspiro[4.5]decane-3-carboxylic acid and the corresponding (2R)-compound and (2S)-compound
21. N-[(2R,S)-3-Acetylthio-2-methylpropanoyl]-(3R)-8-carboxy-1-thia-4-azaspiro[4.5]decane-3-carboxylic acid and the corresponding (2R)-compound and (2S)-compound
22. N-[(2R,S)-3-Mercapto-2-methylpropanoyl]-(3R)-8-carboxy-1-thia-4-azaspiro[4.5]decane-3-carboxylic acid and the corresponding (2R)-compound and (2S)-compound 23. N-[(2R,S)-3-Acetylthio-2-methylpropanoyl]-(3R)-8-oxo-1,8-dithia-4-azaspiro[4.5]decane-3-carboxylic acid and the corresponding (2R)-compound and (2S)-compound 24. N-[(2R,S)-3-Mercapto-2-methylpropanoyl]-(3R)-8-oxo-1,8-dithia-4-azaspiro[4.5]decane-3-carboxylic acid and the corresponding (2R)-compound and (2S)-compound 25. N-[(2R,S)-3-Acetylthio-2-methylpropanoyl]-(3R)-8,8-dioxo-1,8-dithia-4-azaspiro[4.5]decane-3-carboxylic acid and the corresponding (2R)-compound and (2S)-compound 26. N-[(2R,S)-3-Mercapto-2-methylpropanoyl]-(3R)-8,8-dioxo-1,8-dithia-4-azaspiro[4.5]decane-3-carboxylic acid and the corresponding (2R)-compound and (2S)-compound 27. N-[(2R,S)-3-Acetylthio-2-methylpropanoyl]-(6R,S)6-ethoxycarbonyl-1-thia-4-aza-spiro[4.5]decane and the corresponding (2R)-compound and (2S)-compound 28. N-[(2R,S)-3-Mercapto-2-methylpropanoyl]-(6R,S)-6-ethoxycarbonyl-1-thia-4-aza-spiro[4.5]decane and the corresponding (2R)-compound and (2S)-compound 29. N-[(2R,S)-3-Acetylthio-2-methylpropanoyl]-(6R,S)-1-thia-4-azaspiro[4.5]decane-6-carboxylic acid and the corresponding (2R)-compound and (2S)-compound 30. N-[(2R,S)-3-Mercapto-2-methylpropanoyl]-(6R,S)-1-thia-4-azaspiro[4.5]decane-6-carboxylic acid and the corresponding (2R)-compound and (2S)-compound The tables which follow show examples of other compounds according to the invention which are obtained using various starting materials, without restricting the scope of the invention to the compounds mentioned in the tables. The numbering for the radicals in the table corresponds to the general formula I

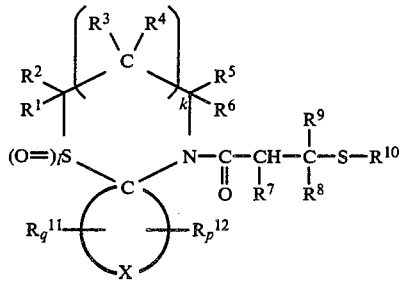

TABLE 1

$k, l, p, q = 0; R^1, R^2, R^5, R^8 = H; R^6 = CO_2H$ (+ = spiro-carbon atom)

| No. | X-containing ring | $R^7$ | $R^9$ | $R^{10}$ | Product |
|---|---|---|---|---|---|
| 1 | tetrahydrothiopyran (+) | H | H | H | spiro[thiopyran-piperidine] with N–C(=O)–CH₂–CH₂–SH, CO₂H |
| 2 | tetrahydrothiopyran (+) | CH₃ | H | C₂H₅ | spiro[thiopyran-piperidine] with N–C(=O)–CH(CH₃)–CH₂–S–CH₂CH₃, CO₂H |
| 3 | tetrahydrothiopyran (+) | Cl | H | –CH₂–C₆H₅ | spiro[thiopyran-piperidine] with N–C(=O)–CH(Cl)–CH₂–S–CH₂–C₆H₅, CO₂H |
| 4 | tetrahydrothiopyran (+) | CH₃ | CH₃ | –C(=O)–C₆H₅ | spiro[thiopyran-piperidine] with N–C(=O)–CH(CH₃)–CH(CH₃)–S–C(=O)–C₆H₅, CO₂H |

TABLE 1-continued $k, l, p, q = 0; R^1, R^2, R^5, R^8 = H; R^6 = CO_2H$

| No. | X-containing ring (+ = spiro-carbon atom) | $R^7$ | $R^9$ | $R^{10}$ | Product |
|---|---|---|---|---|---|
| 5 | thiane (S) | CH$_3$ | H | —C(=O)—CH(CH$_2$-φ)—NH—C(=O)-φ | (dithiane spiro) —N—CH(CO$_2$H)—C(=O)—S—CH$_2$—CH$_2$—S—C(=O)—CH(CH$_3$)—NH—C(=O)-φ with CH$_2$-φ branch |
| 6 | thiane (S) | phenyl | H | H | (dithiane spiro) —N—CH(CO$_2$H)—C(=O)-φ, CH$_2$—CH$_2$—SH |
| 7 | pyran (O) | H | H | —C(=O)-φ | (dioxane-type spiro with O) —N—CH(CO$_2$H)—C(=O)—CH$_2$—CH$_2$—S—C(=O)-φ |
| 8 | pyran (O) | H | phenyl | H | (spiro with O) —N—CH(CO$_2$H)—C(=O)—CH$_2$—CH(φ)—SH |

TABLE 1-continued $k, l, p, q = 0; R^1, R^2, R^5, R^8 = H; R^6 = CO_2H$ (+ = spiro-carbon atom)

| No. | X-containing ring | $R^7$ | $R^9$ | $R^{10}$ | Product |
|---|---|---|---|---|---|
| 9 | tetrahydropyran (spiro) | Cl | H | $-\overset{O}{\underset{\|}{C}}-CH_3$ | spiro thiazolidine-tetrahydropyran with N-C(=O)-CH(Cl)-CH$_2$-S-C(=O)-CH$_3$, CO$_2$H |
| 10 | tetrahydropyran (spiro) | CH$_3$ | H | $-CH_2-$C$_6$H$_5$ | spiro thiazolidine-tetrahydropyran with N-C(=O)-CH(CH$_3$)-CH$_2$-S-CH$_2$-C$_6$H$_5$, CO$_2$H |
| 11 | tetrahydropyran (spiro) | CH$_3$ | H | $-\overset{O}{\underset{\|}{C}}-CH_2-CH_2-\underset{CO_2H}{\overset{\|}{C}H}-NH_2$ | spiro thiazolidine-tetrahydropyran with N-C(=O)-CH(CH$_3$)-CH$_2$-S-C(=O)-CH$_2$-CH$_2$-CH(NH$_2$)-CO$_2$H, CO$_2$H |
| 12 | tetrahydropyran (spiro) | CH$_3$ | CH$_3$ | H | spiro thiazolidine-tetrahydropyran with N-C(=O)-C(CH$_3$)(CH$_3$)-CH(CH$_3$)-SH, CO$_2$H |

TABLE 1-continued
$k, l, p, q = 0; R^1, R^2, R^5, R^8 = H; R^6 = CO_2H$
(+ = spiro-carbon atom)
| No. | X-containing ring | $R^7$ | $R^9$ | $R^{10}$ | Product |
|---|---|---|---|---|---|
| 13 | 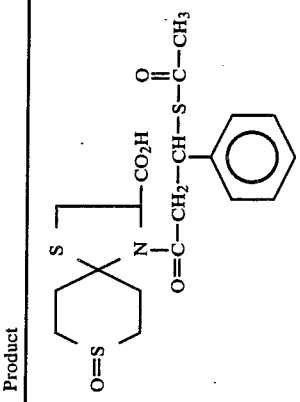 | H | 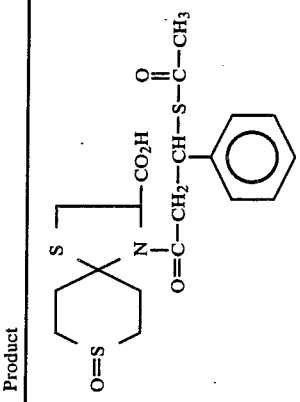 | $-\overset{O}{\underset{\|}{C}}-CH_3$ | 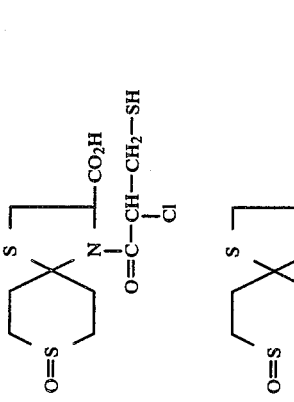 |
| 14 | 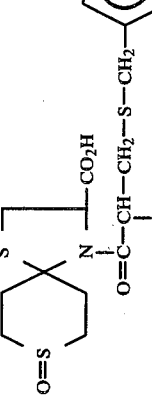 | Cl | H | H | 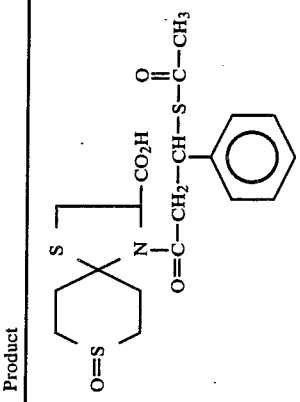 |
| 15 | 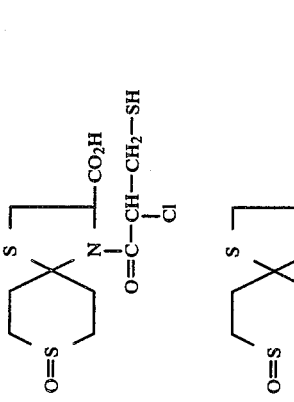 | CH$_3$ | CH$_3$ | —CH$_2$—CH$_3$ | 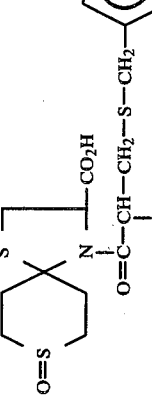 |
| 16 | 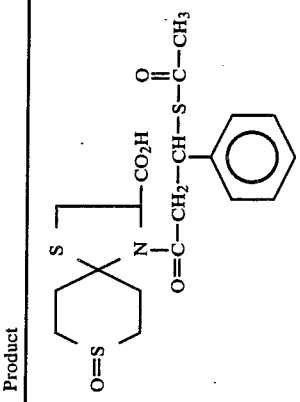 | 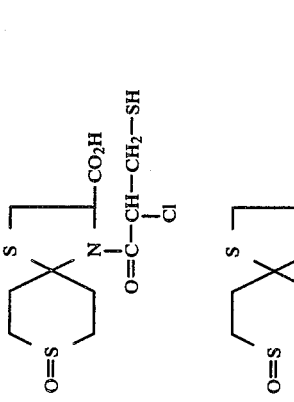 | H | —CH$_2$—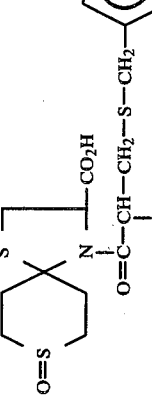 | (structure) |

TABLE 1-continued $k, l, p, q = 0; R^1, R^2, R^5, R^8 = H; R^6 = CO_2H$ (+ = spiro-carbon atom)

| No. | X-containing ring | $R^7$ | $R^9$ | $R^{10}$ | Product |
|---|---|---|---|---|---|
| 17 | tetrahydrothiopyran S-oxide (spiro) | $CH_3$ | H | $-C(=O)-CH(CH_2\phi)-NHC(=O)-$ | spiro tetrahydrothiopyran S-oxide with N-C(=O)-CH(CH_3)-S-CH_2-C(=O)-CH(CH_2\phi)-NH-C(=O)-, CO_2H |
| 18 | tetrahydrothiopyran S-oxide (spiro) | $CH_3$ | H | $-C(=O)-CH_2-CH_2-CH(NH_2)-CO_2H$ | spiro tetrahydrothiopyran S-oxide with N-C(=O)-CH(CH_3)-S-CH_2-CH_2-CH(NH_2)-CO_2H |
| 19 | 4-carboxycyclohexyl (spiro) | H | H | $-C(=O)-\phi$ | 4-HO_2C-cyclohexyl spiro with S, N-C(=O)-CH_2-CH_2-S-C(=O)-\phi, CO_2H |
| 20 | 4-carboxycyclohexyl (spiro) | Cl | H | H | 4-HO_2C-cyclohexyl spiro with S, N-C(=O)-CH(Cl)-CH_2-SH, CO_2H |

4,587,250
TABLE 1-continued
k, l, p, q = 0; R$^1$, R$^2$, R$^5$, R$^8$ = H; R$^6$ = CO$_2$H
| No. | (+ = spiro-carbon atom) X-containing ring | R$^7$ | R$^9$ | R$^{10}$ | Product |
|---|---|---|---|---|---|
| 21 |  | CH$_3$ | CH$_3$ | —C(=O)—CH$_3$ |  |
| 22 |  | H | —C$_6$H$_5$ | —CH$_2$— |  |
| 23 |  | CH$_3$ | H | —C(=O)—CH(CH$_2$C$_6$H$_5$)—NHC(=O)C$_6$H$_5$ | 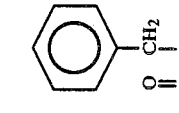 |
| 24 |  | CH$_3$ | H | —C(=O)—CH$_2$—CH$_2$—CH$_2$—NH$_2$ |  |

TABLE 1-continued
$k, l, p, q = 0; R^1, R^2, R^5, R^8 = H; R^6 = CO_2H$
(+ = spiro-carbon atom)
| No. | X-containing ring | $R^7$ | $R^9$ | $R^{10}$ | Product |
|---|---|---|---|---|---|
| 25 | 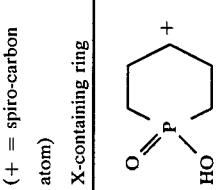 | CH₃ | H |  | 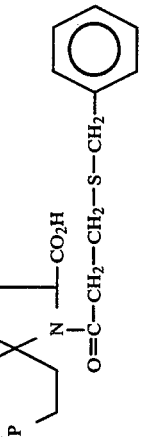 |
| 26 | 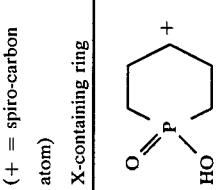 | H | H |  | 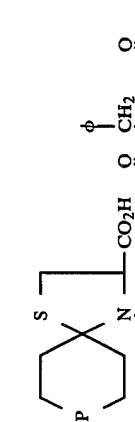 |
| 27 | 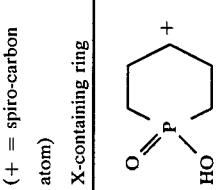 | CH₃ | H | 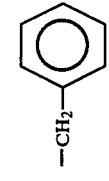 | 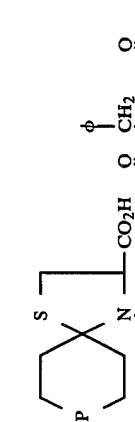 |
| 28 | 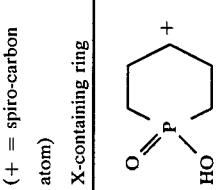 | CH₃ | H | H |  |

TABLE 1-continued
$k, l, p, q = 0; R^1, R^2, R^5, R^8 = H; R^6 = CO_2H$
| No. | (+ = spiro-carbon atom) X-containing ring | $R^7$ | $R^9$ | $R^{10}$ | Product |
|---|---|---|---|---|---|
| 29 | 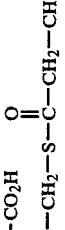 | $CH_3$ | H |  |  |
| 30 |  | Cl | H |  | 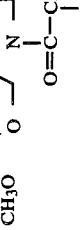 |

TABLE 2
$R^5, R^8, R^9, R^{10} = H; R^6 = CO_2H; R^7 = CH_3$
| No. | $R^1 = R^2$ | $R^3 = R^4$ | k | l | X-containing ring (+ = spiro-carbon atom) | Product |
|---|---|---|---|---|---|---|
| 1 | H | — | 0 | 0 | 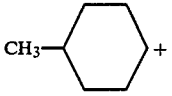 | 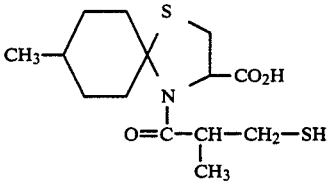 |
| 2 | H | — | 0 | 0 | 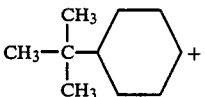 | 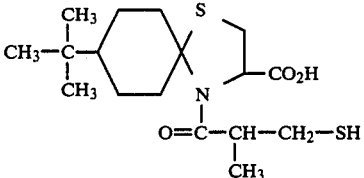 |
| 3 | H | — | 0 | 1 | 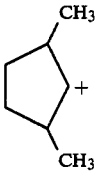 | 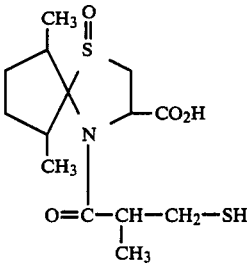 |
| 4 | H | H | 1 | 0 | 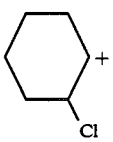 | 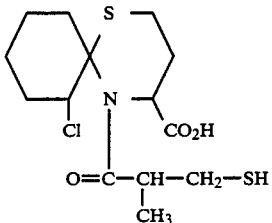 |
| 5 | CH$_3$ | — | 0 | 0 | 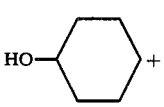 | 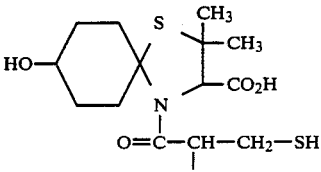 |
| 6 | H | — | 0 | 0 | 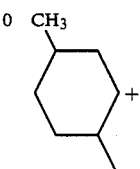 | 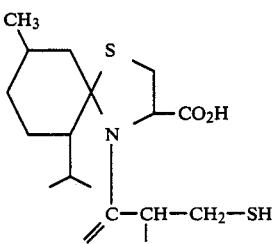 |

TABLE 2-continued
R$^5$, R$^8$, R$^9$, R$^{10}$ = H; R$^6$ = CO$_2$H; R$^7$ = CH$_3$
| No. | R$^1$ = R$^2$ | R$^3$ = R$^4$ | k | l | X-containing ring (+ = spiro-carbon atom) | Product |
|---|---|---|---|---|---|---|
| 7 | H | H | 1 | 0 | 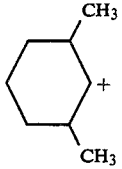 | 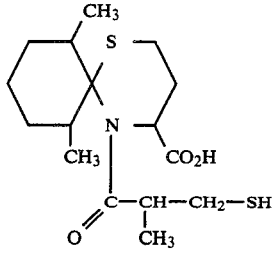 |
| 8 | CH$_3$ | — | 0 | 1 | 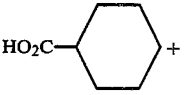 | 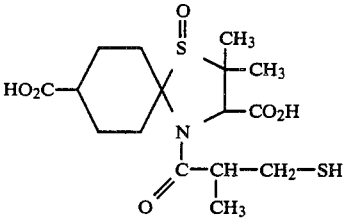 |
| 9 | CH$_3$ | — | 0 | 2 | 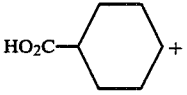 | 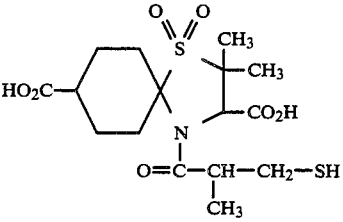 |
| 10 | H | H | 1 | 0 | 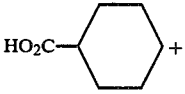 | 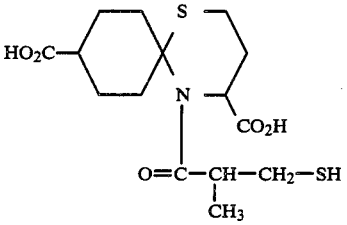 |
| 11 | H | H | 1 | 0 | 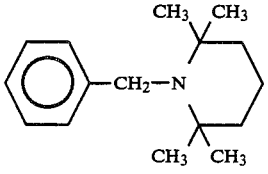 | 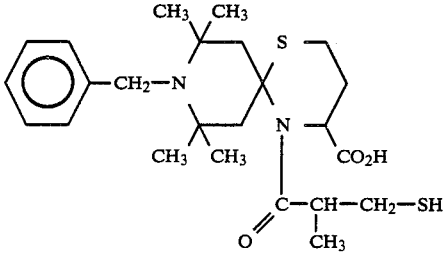 |
| 12 | H | H | 1 | 2 | 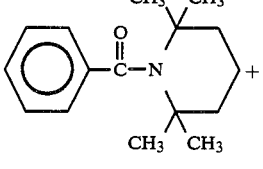 | 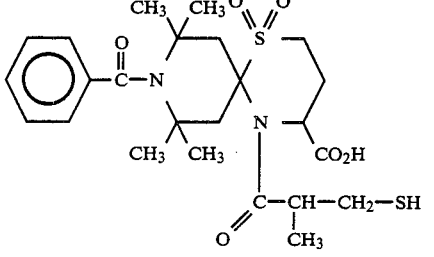 |

TABLE 2-continued $R^5, R^8, R^9, R^{10} = H; R^6 = CO_2H; R^7 = CH_3$

| No. | $R^1 = R^2$ | $R^3 = R^4$ | k | l | X-containing ring (+ = spiro-carbon atom) | Product |
|---|---|---|---|---|---|---|
| 13 | CH₃ | — | 0 | 1 | | |
| 14 | H | — | 0 | 0 | | |
| 15 | CH₃ | — | 0 | 0 | | |
| 16 | CH₃ | — | 0 | 0 | | |
| 17 | H | H | 1 | 1 | | |
| 18 | H | — | 0 | 2 | | |
| 19 | H | — | 0 | 0 | | |

TABLE 2-continued
$R^5, R^8, R^9, R^{10} = H; R^6 = CO_2H; R^7 = CH_3$
| No. | $R^1 = R^2$ | $R^3 = R^4$ | k | l | X-containing ring (+ = spiro-carbon atom) | Product |
|---|---|---|---|---|---|---|
| 20 | CH₃ | — | 0 | 0 | 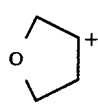 | 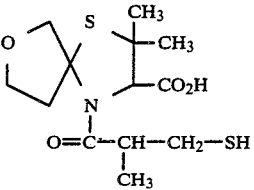 |
| 21 | H | H | 1 | 0 | 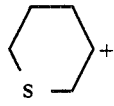 | 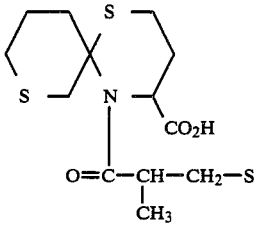 |
| 22 | H | — | 0 | 1 | 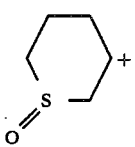 | 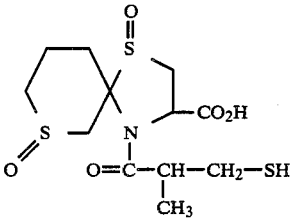 |
| 23 | CH₃ | — | 0 | 0 | 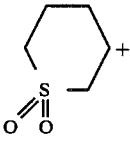 | 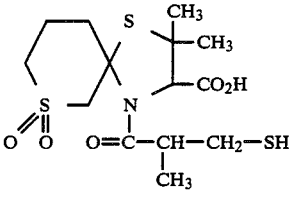 |
| 24 | H | — | 0 | 0 | 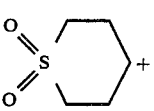 | 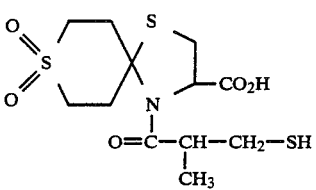 |
| 25 | CH₃ | — | 0 | 0 | 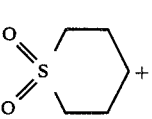 | 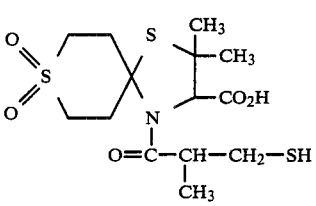 |
| 26 | H | — | 0 | 0 | 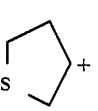 | 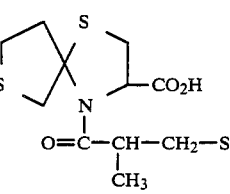 |

TABLE 2-continued
R⁵, R⁸, R⁹, R¹⁰ = H; R⁶ = CO₂H; R⁷ = CH₃
| No. | R¹ = R² | R³ = R⁴ | k | l | X-containing ring (+ = spiro-carbon atom) | Product |
|---|---|---|---|---|---|---|
| 27 | H | H | 1 | 1 | 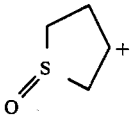 | 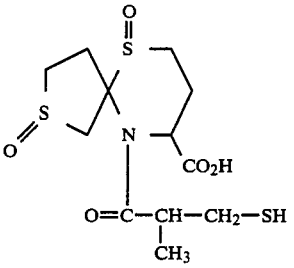 |
| 28 | CH₃ | — | 0 | 0 | 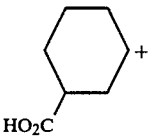 | 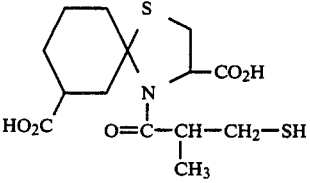 |
| 29 | H | — | 0 | 2 | 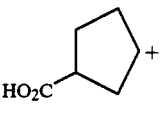 | 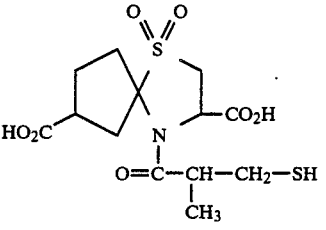 |
| 30 | H | — | 0 | 0 | 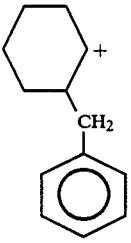 | 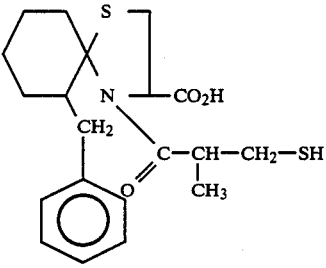 |

TABLE 3
$k, l = 0, R^5, R^8, R^9 = H$
| No. | $R^1-R^2$ | $R^6$ | $R^7$ | $R^{10}$ | X-containing ring (+ = spiro-carbon atom) | Product |
|---|---|---|---|---|---|---|
| 1 | H | CO$_2$H | CH$_3$ | 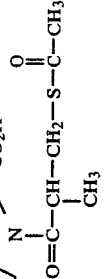 |  | 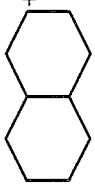 |
| 2 | CH$_3$ | CO$_2$H | Cl | H | 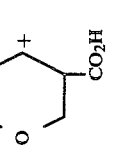 | 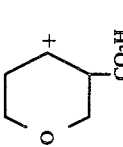 |
| 3 | H | H | CH$_3$ | H | 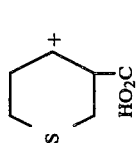 |  |
| 4 | H | H | Cl |  | | |

TABLE 3-continued $k, l = O, R^5, R^8, R^9 = H$

| No. | $R^1$-$R^2$ | $R^6$ | $R^7$ | $R^{10}$ | X-containing ring (+ = spiro-carbon atom) | Product |
|---|---|---|---|---|---|---|
| 5 | H | H | CH$_3$ | H | | |
| 6 | H | H | CH$_3$ | H | | |
| 7 | H | H | | | | |
| 8 | CH$_3$ | CO$_2$H | Cl | | | |

TABLE 3-continued $k, l = O, R^5, R^8, R^9 = H$

| No. | $R^1$-$R^2$ | $R^6$ | $R^7$ | $R^{10}$ | X-containing ring (+ = spiro-carbon atom) | Product |
|---|---|---|---|---|---|---|
| 9 | H | $CO_2H$ | $CH_3$ | H | (bicyclic amine with $CH_3$-N+) | (bicyclic thia-amide with $CH_3$-N, $CO_2H$, $O=C-CH-CH_2-SH$, $CH_3$) |
| 10 | $CH_3$ | $CO_2H$ | $CF_3$ | $-CH_2-\phi$ | (bicyclic cation) | (bicyclic S,N ring with $CH_3$, $CH_3$, $CO_2H$, $O=C-CH-CH_2-S-CH_2-\phi$, $CF_3$) |
| 11 | H | $CO_2H$ | $CH_3$ | H | (bicyclic cation) | (bicyclic S,N ring with $CO_2H$, $O=C-CH-CH_2-SH$, $CH_3$) |
| 12 | $CH_3$ | $CO_2H$ | $-CH_2-\phi$ | cyclopentyl-C(=O)- with 4-(guanidinocarbonyl)phenyl-NH-C(=O)- | $(CH_3)_2C$-spiro-bicyclic+ | (spiro bicyclic S,N system with $CH_3$, $CH_3$, $C(CH_3)_2$, phenyl-NH with guanidinocarbonyl, cyclopentyl-C(=O)-S-CH_2-CH-C(=O)-N, $CH_2\phi$) |

TABLE 3-continued $k, l = O, R^5, R^8, R^9 = H$

| No. | $R^1$, $R^2$ | $R^6$ | $R^7$ | $R^{10}$ | X-containing ring (+ = spiro-carbon atom) | Product |
|---|---|---|---|---|---|---|
| 13 | H | -C(=O)-O-CH(φ)-CO₂H | CH₃ | -C(=O)-φ | tetrahydrothiopyran-S-oxide (+) | spiro product with S=O ring, N-C(=O)-CH(CH₃)-S-CH₂-CH₂-C(=O)-φ and benzyl ester CH-O-C(=O)-CH(φ)-CO₂H |
| 14 | H | -C(=O)-O-CH(φ)-CO₂H | CH₃ | H | 4-carboxycyclohexyl (+) | cyclohexane with HO₂C, N-C(=O)-CH(CH₃)-CH₂-SH, and benzyl ester |
| 15 | H | -C(=O)-NH-C₆H₄-C(=O)-NHC(=NH)NH₂ | CH₃ | -C(=O)-CH(CH₂φ)-NH-C(=O)-φ | tetrahydropyran (+) | spiro product with O ring, amide linkages to phenyl-C(=O)-NHC(=NH)NH₂ and -C(=O)-CH(CH₃)-S-CH₂-CH(NH-C(=O)-φ)-CH₂-φ |

The compounds of the general formula I are pharmacologically useful substances. They have liver-protective, antiphlogistic, analgesic, antilipemic, antiarteriosclerotic, antidiabetic, antihypertensive, platelet aggregationinhibiting, vasodilatory and sedative actions. The present invention thus also relates to a medicament as claimed in the patent claims, for use on humans and animals. Use on humans is preferred.

The excellent antihypertensive action of compounds of the general formula I is surprising and is to be emphasized.

When the compounds of the general formula I according to the invention were investigated on rabbits, the substances investigated proved to be particularly effective antihypertensive agents on both intravenous and oral administration. Doses of from 0.2 to 200 mg/kg administered orally led, after 2 hours, to a suppression of the rise in blood pressure (20 mm Hg) caused by intravenous infusion of 0.01 mg/minute of Angiotensin I.

On rats in which high blood pressure had been imposed by artificial aortic stenosis, doses of from 0.2 to 200 mg/kg administered orally led to an average reduction in the mean arterial blood pressure of about 20 mm Hg after 2 hours.

The compounds according to the invention can be administered in a large number of pharmaceutical formulation forms and dosages, for example tablets, coated tablets, capsules, liquid formulations to be taken orally, ointments, gels, plasters, injection solutions or sprays, and conventional auxiliaries and excipients which are compatible with the compounds according to the invention can be used. The dosages can be from 10 to 500 mg of a compound of the formula I or its salt per dose unit, with administration of from 1 to 4 dose units daily.

The examples which follow serve to illustrate the invention, without restricting it thereto.

EXAMPLE 1

(2R,S)-3-Acetylthio-2-methylpropanoic acid 50 g of thioacetic acid and 43 g of methacrylic acid are mixed, and 1 g of azobisisobutyronitrile is added. The mixture is heated to 80° C. for 3 hours, while stirring, and is subjected to fractional distillation in vacuo to give 40 g of colorless liquid of boiling point 141° C./6 mm Hg.

IR: $\nu = 1745, 1700$ cm$^{-1}$.

EXAMPLE 2

(2R,S)-3-Acetylthio-2-methylpropanoyl chloride 29.8 g of the product from Example 1, 25.7 g of thionyl chloride and a few drops of dimethylformamide are mixed and are stirred at room temperature for 24 hours, with exclusion of moisture. The excess thionyl chloride is first removed under reduced pressure and the mixture is then subjected to fractional distillation to give 26 g of colorless liquid of boiling point 65° C./2 mm Hg.

IR: $\nu = 1790, 1700$ cm$^{-1}$.

EXAMPLE 3

(2S)-3-Acetylthio-2-methylpropanoic acid 50 g of the product from Example 1 are suspended in 500 ml of acetonitrile, and 91 g of cinchonidine are added. The mixture is stirred, while boiling, for 30 minutes and is filtered hot and left to crystallize at 4° C. 100 g of the precipitate are dissolved again in 350 ml of acetonitrile by heating and the solution is made to crystallize at 4° C. This procedure is repeated twice more to give 15 g of colorless crystals. The crystals are dissolved in hot water and the solution is left to cool, acidified to pH 2 and extracted with ethyl acetate. The extract is dried over anhydrous sodium sulfate and the ethyl acetate is removed under reduced pressure. The oil which remains is distilled under reduced pressure to give 5 g of colorless liquid of boiling point 141° C./6 mm Hg.

IR: $\nu = 1745, 1700$ cm$^{-1}$.

$[\alpha]_D^{25} = -33°$ C. (ethanol).

EXAMPLE 4

(2S)-3-Acetylthio-2-methylpropanoyl chloride

The product from Example 3 is used instead of the product from Example 1 in the process according to Example 2 to give the title compound of boiling point 65° C./2 mm Hg.

IR: $\nu = 1790, 1700$ cm$^{-1}$.

EXAMPLE 5

(3R, 3'R)-4,4'-[3,3'-Dithiobis[2-(R,S)-2-methylpropanoyl]]-bis-[1-thia-4-azaspiro[4.5]decane-3-carboxylic acid)

3.43 g of N-[(2R,S)-3-acetylthio-2-methylpropanoyl]-(3R)-1-thia-4-azaspiro[4.5]decane-3-carboxylic acid are suspended in 30 ml of 12.5% strength ammonia and the suspension is stirred at room temperature for 3 hours, during which time oxygen is passed through the reaction mixture. The mixture is diluted with 50 ml of water, the pH is brought to 7.0 by dropwise addition of 4 N HCl and the mixture is extracted with methylene chloride. The extract is dried over sodium sulfate, the solvent is removed under reduced pressure and the residue is recrystallized from water/ethanol to give 2.8 g of colorless crystals of melting point 168° C.

Thin layer chromatogram: 1 spot, RF=0.45 (ethyl acetate).

Nitrogen content: 4.45% (theory: 4.63%).

IR: $\nu = 2940, 2860, 1720, 1640$ cm$^{-1}$.

EXAMPLE 6

N-[(2R,S)-3-Acetylthio-2-methylpropanoyl]-(3R)-2,2-dimethyl-1-thia-4-azaspiro[4.5]decane-3-carboxylic acid 4.58 g of (3R)-2,2-dimethyl-1-thia-4-azaspiro[4.5]decane-3-carboxylic acid are dissolved in 40 ml of absolute tetrahydrofuran. 2.22 g of triethylamine are added, the mixture is cooled to 0° C., with exclusion of moisture, and a solution of 3.6 g of the product from Example 2 in 20 ml of absolute tetrahydrofuran is added dropwise. The mixture is stirred at 0° C. for 2 hours and at room temperature for 16 hours. The solvent is removed under reduced pressure, 100 ml of water are added, the pH is brought to 7 and the mixture is extracted with methylene chloride. The pH is brought to 3 by dropwise addition of 1 N HCl and the mixture is extracted with ethyl acetate. The extract is dried over anhydrous sodium sulfate and is evaporated to dryness on a rotary evaporator. The colorless residue is recrystallized from water/methanol to give 4 g of the title compound of melting point 166° C.

Thin layer chromatogram: 1 spot, RF=0.5 (ethanol).

Nitrogen content: 3.50% (theory: 3.75%).

IR: $\nu = 1730, 1690, 1650$ cm$^{-1}$.

EXAMPLE 7

N-[(2R,S)-3-Mercapto-2-methylpropanoyl]-(3R)-2,2-dimethyl-1-thia-4-azaspiro[4.5]decane-3-carboxylic acid 3.71 g of the product from Example 6 are suspended in 15 ml of water which is saturated with nitrogen, and 15 ml of concentrated ammonia are added. The mixture is stirred at room temperature for 1 hour, while passing in nitrogen, and is diluted with 50 ml of nitrogen-saturated water. The pH is brought to 7 by dropwise addition of 4 N HCl and the mixture is extracted with ether. The aqueous phase is immediately brought to pH 3 and is extracted with ethyl acetate. The extract is dried over anhydrous sodium sulfate and concentrated to dryness under reduced pressure. The resulting oil is dissolved in hot ethanol, and nitrogen-saturated water is added until the mixture starts to become turbid. 1.7 g of colorless crystals of melting point 158° C. are obtained.

Thin layer chromatogram: 1 spot, RF=0.4 (ethanol).
Nitrogen content: 4.08% (theory: 4.22%).
IR: $v$=2930, 2860, 2580, 1740, 1600 cm$^{-1}$.
MS: 332 (M+1).

EXAMPLE 8

Methyl N-[(2R,S)-3-acetylthio-2-methylpropanoyl]-(3R)-8-phenyl-1-thia-4-azaspiro[4.5]decane-3-carboxylate 3.27 g of methyl 3-(R)-8-phenyl-1-thia-4-azaspiro[4.5]decane-3-carboxylate hydrochloride are used as the starting compound in a process as described in Example 6 to give 3.5 g of the title compound from the neutral extract. The product is recrystallized from ethanol/water to give 3 g of slightly yellowish needles.

EXAMPLE 9

Methyl N-[(2R,S)-3-mercapto-2-methylpropanoyl]-(3R)-8-phenyl-1-thia-4-azaspiro[4.5]decane-3-carboxylate 4.32 g of the product from Example 8 are used in a process as described in Example 7 to give 2.3 g of the title compound.

EXAMPLE 10

N-[(2R,S)-3-Acetylthio-2-methylpropanoyl]-(3R)-8-oxa-1-thia-4-azaspiro[4.5]decane-3-carboxylic acid 4.06 g of 3-(R)-8-oxa-1-thia-4-azaspiro[4.5]decane-3-carboxylic acid are used as the starting compound in a process as described in Example 6 to give 2 g of the title compound of melting point 167° C.

Thin layer chromatogram: 1 spot, RF=0.53 (ethanol).
Nitrogen content: 4.18% (theory: 4.06%).
IR: $v$=2965, 2930, 2855, 1740, 1690, 1680, 1602 cm$^{-1}$.

EXAMPLE 11

N-[(2R,S)-3-Mercapto-2-methylpropanoyl]-(3R)-8-oxa-1-thia-4-azaspiro[4.5]decane-3-carboxylic acid 3.45 g of the product from Example 10 are used in a process as described in Example 7 to give 2.0 g of the title compound of melting point 163° C.

Thin layer chromatogram: 1 spot, RF=0.45 (ethanol).
Nitrogen content: 4.63% (theory: 4.59%).

EXAMPLE 12

4-[(2R,S)-3-Acetylthio-2-methylpropanoyl]-(3R)-8-methyl-1-thia-4,8-diazaspiro[4.5]decane-3-carboxylic acid 4.32 g of 3-(R)-8-methyl-1-thia-4,8-diazaspiro[4.5]decane-3-carboxylic acid are suspended in 70 ml of dry tetrahydrofuran, and 4.04 g of triethylamine are added. 3.61 g of the product from Example 2 are then added dropwise and the mixture is stirred at 50° C. for 3 hours. The precipitate is filtered off with suction. Further colorless solid is obtained from the mother liquor by concentration and addition of acetone. The product is recrystallized from acetonitrile until no further triethylammonium chloride is present. 2.66 g of colorless powder of melting point 226° C., recrystallized from water/acetone, are obtained.

IR: $v$=2970, 2930, 1690, 1647 cm$^{-1}$.

EXAMPLE 13

4-[(2R,S)-3-Mercapto-2-methylpropanoyl]-(3R)-8-methyl-1-thia-4,8-diazaspiro[4.5]decane-3-carboxylic acid 2.5 ml of water and 1.8 ml of 12.5% strength ammonia are added to 1.8 g of the product from Example 12. The mixture is stirred at room temperature for 3 hours under a nitrogen atmosphere. 20 ml of water are added and the mixture is extracted with ether. The aqueous phase is acidified and extracted with ethyl acetate. The aqueous phase is concentrated to dryness and the residue is chromatographed on silica gel (eluant: methanol). 0.9 g of a colorless oil which slowly solidifies to give a product of melting point 204° C. results.

Thin layer chromatogram: 1 spot, RF=0.12 (ethanol/formic acid=9:1).
IR: $v$=2540, 1730, 1690, 1640 cm$^{-1}$.

EXAMPLE 14

N-[(2R,S)-3-Acetylthio-2-methylpropanoyl]-(3R)-1,8-dithia-4-azaspiro[4.5]decane-3-carboxylic acid 2.19 g of 3(R)-1,8-dithia-4-azaspiro[4.5]decane-3-carboxylic acid are dissolved in 30 ml of dry tetrahydrofuran, and 2.77 ml of triethylamine are added. 1.81 g of the product from Example 2 are added dropwise, while stirring, and the mixture is stirred at 50° C. for 3 hours, allowed to cool, filtered and evaporated to dryness under reduced pressure. The residue is dissolved in 40 ml of 1 N HCl and the solution is extracted with ethyl acetate. The organic phase is dried and evaporated to give 3.65 g of a colorless oil. The oil is chromatographed on silica gel in methylene chloride/formic acid (40:1). After evaporation under reduced pressure, 0.9 g of colorless crystals is obtained. Recrystallization from carbon tetrachloride/acetone gives 2 fractions of melting point 198° C.$\hat{=}$A and melting point 138° C.$\hat{=}$B.

MS (A) 364 (M+1), MS (B) 364 (M+1).
IR (A=B): $v$=1735, 1690, 1680, 1610 cm$^{-1}$.

EXAMPLE 15

N-[(2R,S)-3-Mercapto-2-methylpropanoyl]-(3R)-1,8-dithia-4azaspiro[4.5]decane-3-carboxylic acid 0.3 g of the product A from Example 14 is dissolved in 0.5 ml of water and 0.3 ml of 12.5% strength ammonia, and the mixture is stirred under nitrogen at room temperature for 2 hours. The mixture is diluted with water to 20 ml, acidified to pH 1 with 2 N HCl and extracted with ethyl acetate. The extract is dried over sodium sulfate and evaporated to give 0.2 g of colorless crystals. The crystals are recrystallized from chloroform to give a product of melting point 186° C.

IR: ν=2560, 1730, 1600 cm$^{-1}$.

EXAMPLE 16

The product from Example 4 is used as one of the starting compounds instead of the product from Example 2 in the reactions described in Examples 6, 8, 10, 12 and 14 to give, in a similar manner, N-[(2S)-3-acetylthio-2-methylpropanoyl]-(3R)-2,2-dimethyl-1-thia-4-azaspiro[4.5]decane-3-carboxylic acid, methyl N-[(2S)-3-acetylthio-2-methylpropanoyl]-(3R)-8-phenyl-1-thia-4-azaspiro[4.5]decane-3-carboxylate, N-[(2S)-3-acetylthio-2-methylpropanoyl]-(3R)-8-oxa-1-thia-4-azaspiro[4.5]decane-3-carboxylic acid, 4-[(2S)-3-acetylthio-2-methylpropanoyl]-(3R)-8-methyl-1-thia-4,8-diazaspiro[4.5]decane-3-carboxylic acid and N-[(2S)-3-acetylthio-2-methylpropanoyl]-(3R)-1,8-dithia-4-azaspiro[4.5]decane-3-carboxylic acid.

EXAMPLE 17

The compounds obtained in Example 16 are reacted as described in Example 13 to give N-[(2S)-3-mercapto-2-methylpropanoyl]-(3R)-2,2-dimethyl-1-thia-4-azaspiro[4.5]decane-3-carboxylic acid, methyl N-[(2S)-3-mercapto-2-methylpropanoyl]-(3R)-8-phenyl-1-thia-4-azaspiro[4.5]decane-3-carboxylate, N-[(2S)-3-mercapto-2-methylpropanoyl]-(3R)-8-oxa-1-thia-4-azaspiro[4.5]-decane-3-carboxylic acid, 4-[(2S)-3-mercapto-2-methylpropanoyl]-(3R)-8-methyl-1-thia-4,8-diazaspiro[4.5]-decane-3-carboxylic acid and N-[(2S)-3-mercapto-2-methylpropanoyl]-(3R)-1,8-dithia-4-azaspiro[4.5]decane-3-carboxylic acid.

EXAMPLE 18

4-[(2R,S)-3-Acetylthio-2-methylpropanoyl]-(3R)-8-benzoyl-1-thia-4,8-diazaspiro[4.5]decane-3-carboxylic acid 6.12 g of 3-(R)-8-benzoyl-1-thia-4,8-diazaspiro[4.5]-decane-3-carboxylic acid are dissolved in 50 ml of dry tetrahydrofuran, and 2.22 g of triethylamine are added. 3.6 g of 3-acetylthio-2-(R,S)-methylpropanoyl chloride, dissolved in 20 ml of tetrahydrofuran, are added dropwise, while cooling with ice. The mixture is stirred at 0° C. for 2 hours and at room temperature for 48 hours and is filtered and concentrated to 10 ml. The concentrate is taken up in 50 ml of water and the mixture is brought to pH 7.0 and extracted with ether. The aqueous phase is brought to pH 3.0 and extracted with ethyl acetate. The ethyl acetate phase is dried over sodium sulfate and concentrated under reduced pressure. 5 g of a colorless powder result, and are recrystallized from ethanol/water to give colorless needles.

Nitrogen content: 6.13% (theory: 6.22%).
IR: ν=2980, 1740, 1690, 1650, 1630 cm$^{-1}$.

EXAMPLE 19

4-[(2R,S)-3-Mercapto-2-methylpropanoyl]-(3R)-8-benzoyl-1-thia-4,8-diazaspiro[4.5]decane-3-carboxylic acid The product from Example 18 is reacted as described in Example 13 to give 1 g of the title compound.

EXAMPLE 20

Recipe for the preparation of tablets 1,000 tablets are prepared from the compounds below in the manner described below. One tablet contains 100 mg of N-[(2S)-3-mercapto-2-methylpropanoyl]-(3R)-1,8-dithia-4-azaspiro[4.5]decane-3-carboxylic acid as the active ingredient.

(1) N-[(2S)-3-Mercapto-2-methylpropanoyl]-(3R)-1,8-dithia-4-azaspiro[4.5]decane-3-carboxylic acid: 100 g
(2) Lactose: 263 g
(3) Microcrystalline cellulose: 120 g
(4) Maize starch: 60 g
(5) Magnesium stearate: 7 g (1) and (2) are mixed, (3) and (4) are mixed in, (5) is added finally, the components are mixed and the mixture is pressed directly.

EXAMPLE 21

(3R)-8-Oxa-1-thia-4-azaspiro[4.5]decane-3-carboxylic acid

A suspension of 5.6 g of L-cysteine and 5 g of tetrahydropyranone in 50 ml of ethanol is heated to the boiling point, and water is added until a clear solution is obtained (about 20 ml). The solution is refluxed for 5 hours and concentrated to dryness. The colorless residue is recrystallized from water to give 9.5 g of colorless needles of melting point 140° C. (decomposition).

Thin layer chromatogram: 1 spot, RF=0.4 (butanol/glacial acetic acid/water=6:2:2).
Nitrogen content: 6.88% (theory: 6.89%).
IR: ν=3340, 2980, 1620 cm$^{-1}$.

EXAMPLE 22

Ethyl (6 R,S)-1-thia-4-azaspiro[4.5]decane-6-carboxylate hydrochloride 8.5 g of ethyl cyclohexanone-2-carboxylate and 5.5 g of cysteamine hydrochloride are dissolved in 100 ml of a 1:1 (volume/volume) mixture of ethanol and water, the pH is brought to 5 and the mixture is refluxed for 5 hours. The solvent is removed under reduced pressure. The solid residue is recrystallized from isopropanol to give 1.1 g of colorless crystals of melting point 174° C.

Nitrogen content: 5.1% (theory: 5.28%)
Thin layer chromatogram: RF=0.61 (ethanol/formic acid 10:1).

EXAMPLE 23

Methyl (3R)-8-phenyl-1-thia-4-azaspiro[4.5]decane-3-carboxylate hydrochloride 4.35 g of 4-phenylcyclohexanone and 4.28 g of L-cysteine methyl ester hydrochloride are suspended in 40 ml of methanol and the suspension is refluxed for one hour. When the suspension is cooled, the product separates out as colorless crystals. The crystals are recrystallized from isopropanol to give 6.67 g of colorless crystals of melting point 216° C.

Nitrogen content: 4.32% (theory: 4.25%).
Thin layer chromatogram: 1 spot (isopropanol/formic acid 8:1).

EXAMPLE 24

Methyl (3R)-8-tert.-butyl-1-thia-4-azaspiro[4.5]decane-3-carboxylate hydrochloride 3.55 g of 4-tert.-butylcyclohexanone and 4.28 g of L-cysteine methyl ester hydrochloride are suspended in 40 ml of methanol and the suspension is refluxed for one hour. The solvent is evaporated off under reduced pressure and the residue is recrystallized from isopropanol to give 6.4 g of colorless crystals of melting point 198° C. (decomposition).

Nitrogen content: 4.74 (theory: 4.52%).

Thin layer chromatogram: RF=0.75 (chloroform/methanol=9:1).

EXAMPLE 25

(3R)-1,8-Dithia-4-azaspiro[4.5]decane-3-carboxylic acid 5.22 g of L-cysteine and 5 g of tetrahydrothiopyranone are suspended in 50 ml of toluene and the suspension is boiled, using a water separator, until the theoretical amount of water has been separated off. When the suspension is cooled, the product separates out as a light yellow precipitate, which is recrystallized from methanol/water to give 6.9 g of light yellow crystals of melting point 196° C.

| Analysis: | % C | % H | % N | % S |
|---|---|---|---|---|
| calculated: | 44.03 | 5.50 | 6.42 | 29.35 |
| found: | 43.87 | 5.93 | 6.31 | 29.12 |

EXAMPLE 26

Methyl (3R)-8-methyl-1-thia-4-azaspiro[4.5]decane-3-carboxylate hydrochloride 34.3 g of L-cysteine methyl ester hydrochloride and 15.4 ml of 4-methylcyclohexanone are suspended in 70 ml of methanol and the suspension is refluxed for 3 hours. The suspension is concentrated to dryness under reduced pressure and the residue is recrystallized from isopropanol/methanol to give 25 g of colorless crystals of melting point 180° C.

Nitrogen content: 5.35% (theory: 5.28%).

EXAMPLE 27

Spiro[8-methyl-8-azabicyclo[3.2.1]octane-3,2'-(4'R)-1'-thia-3'-azacyclopentane-4'-carboxylic acid]

10 g of tropinone and 8.7 g of L-cysteine are dissolved in a 50:50 (volume/volume) mixture of ethanol and water. The solution is refluxed for 5 hours and concentrated to dryness under reduced pressure and the residue is recrystallized from ethanol/water to give 12 g of a brown solid of melting point >280° C.

Nitrogen content: 11.38% (theory: 11.57%)

IR: ν=3420, 2920, 1620 cm$^{-1}$.

We claim:

1. A mercaptoacyl derivative of a thiazaspiro compound

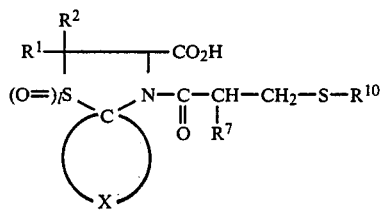

and salts thereof with physiologically acceptable bases, in which the connecting lines shown in the formula between the spiro-carbon atom and X are lower alkylene groups of identical or different chain lengths, and the X-containing ring thereby formed contains 5 or 6 ring members and X can occupy any positions except the positions immediately adjacent to the spiro-carbon atom, $R^1$ and $R^2$ independently of one another are hydrogen or methyl, $R^7$ is hydrogen or lower alkyl with not more than 6 carbon atoms, $R^{10}$ is hydrogen, lower alkanoyl with not more than 6 carbon atoms or benzoyl, X is oxygen, sulfur,

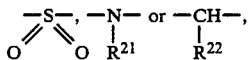

in which $R^{21}$ is lower alkanoyl with not more than 6 carbon atoms or benzoyl, $R^{22}$ is hydrogen, lower alkyl with not more than 6 carbon atoms or phenyl, 1 is 0 or 1, with the proviso that is X is

1 is 1.

2. A compound in accordance with claim 1 in which $R^1$ and $R^2$ are hydrogen, $R^7$ is methyl and the X-containing ring has six ring members and X is linked to the spiro-carbon atom by two lower alkylene radicals of identical chain length, with the proviso that if X is

1 is 1.

3. A compound as claimed in claim 2, in which X is oxygen.

4. A compound as claimed in claim 2, in which X is sulfur.

5. A compound as claimed in claim 2, in which X is

6. A compound as claimed in claim 2, in which X is

7. A compound as claimed in claim 2, in which X is

8. A compound as claimed in claim 2, in which l is other than zero.

9. A compount as claimed in claim 1, in which R¹, R² and R⁷ are methyl, the X-containing ring has six ring members and X is linked to the spiro-carbon atom by two lower alkylene radicals of identical chain lengths.

10. A compound as claimed in claim 9, in which l is other than zero.

11. A method of therapy for reducing high blood pressure in humans or animals comprising administering one or more compounds in accordance with claim 1.

12. A medicament for reducing high blood pressure in humans or animals which comprises one or more compounds in accordance with claim 1 together with conventional excipients and auxiliaries.

13. A medicament for reducing high blood pressure in humans or animals comprising at least one of the compounds or claim 1.

* * * * *